United States Patent [19]

Bey et al.

[11] 4,418,077

[45] Nov. 29, 1983

[54] FLUORINATED AMINO-BUTYRIC ACID AND DIAMINOBUTANE DERIVATIVES

[75] Inventors: Philippe Bey, Strasbourg, France; Fritz Gerhart, Kehl-Leutesheim, Fed. Rep. of Germany; Michel Jung, Illkirch-Graffenstaden; Daniel Schirlin, Bischeim, both of France

[73] Assignee: Merrell Toraude et Compagnie, Strasbourg, France

[21] Appl. No.: 295,060

[22] Filed: Aug. 21, 1981

[30] Foreign Application Priority Data

Aug. 23, 1980 [GB] United Kingdom ............... 8027504

[51] Int. Cl.$^3$ .................. C07C 87/22; C07C 87/28; C07C 101/24; A61K 31/13
[52] U.S. Cl. ............................... 424/309; 564/510; 424/311; 424/320; 424/324; 424/325; 424/330; 560/39; 560/40; 560/41; 560/169; 560/170; 560/172; 562/444; 562/448; 562/449; 562/561; 562/565; 562/574; 564/155; 564/159; 564/164; 564/165; 564/170; 564/182; 564/183; 564/185; 564/196; 564/197; 564/198; 564/209; 564/220; 564/224; 564/367
[58] Field of Search .............. 560/39, 169, 40, 41; 560/172, 170; 562/574, 561, 444, 448, 449, 565; 564/164, 165, 182, 183, 184, 185, 170, 196, 209, 197, 218, 220, 215, 367, 510, 155, 159, 224; 424/309, 311, 319, 320, 324, 325, 330

[56] References Cited

U.S. PATENT DOCUMENTS

| 3,169,133 | 2/1965 | Ayer | 564/510 |
| 4,134,918 | 1/1979 | Bey | 564/510 |
| 4,264,590 | 4/1981 | Chu | 562/574 |
| 4,326,071 | 4/1982 | Bey | 562/574 |

FOREIGN PATENT DOCUMENTS

56-55359  5/1981  Japan ........................ 562/574

OTHER PUBLICATIONS

Silverman, Biochem., 15, pp. 4718-4723, (1976).

Walsh, "Enzyme-Activated Irreversible Inhibitors," pp. 177-185, (1978).

*Primary Examiner*—Michael L. Shippen
*Attorney, Agent, or Firm*—David E. Frankhouser; Raymond A. McDonald; Gary D. Street

[57] ABSTRACT

Fluorinated aminobutyric acid and diaminobutane compounds in vivo are inhibitors of gamma-aminobutyric acid transaminase and have the following formula:

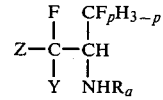

wherein:
Y represents hydrogen or fluorine;
Z represents —CH$_2$NR$_1$R$_2$, where R$_1$ and R$_2$ are as defined below, or —COR$_3$ where R$_3$ is as defined below;
R$_a$ represents hydrogen or R$_4$, where R$_4$ is as defined below;
R$_1$ represents hydrogen, C$_1$-C$_6$ alkyl or phenyl-(C$_1$-C$_4$ alkyl);
R$_2$ represents hydrogen, C$_1$-C$_6$ alkyl, phenyl-(C$_1$-C$_4$ alkyl) or, when R$_a$ is hydrogen, R$_4$, where R$_4$ is as defined below;
R$_3$ represents hydroxy, or when R$_a$ is hydrogen, C$_1$-C$_8$ alkoxy, —NR$_5$R$_6$, where R$_5$ and R$_6$ are as defined below, or an aminocarboxylic acid residue derived by removal of an hydrogen atom from the amino moiety of an L-aminocarboxylic acid;
each R$_4$, independently, represents C$_2$-C$_5$ alkylcarbonyl, phenylcarbonyl, phenyl-(C$_1$-C$_4$ alkyl)-carbonyl, or an aminocarboxylic acid residue derived by removal of an hydroxy group from the carboxy moiety of an L-aminocarboxylic acid;
R$_5$ and R$_6$, independently, represent hydrogen or C$_1$-C$_4$ alkyl; and
P represents 1 or 2.

20 Claims, No Drawings

FLUORINATED AMINO-BUTYRIC ACID AND DIAMINOBUTANE DERIVATIVES

FIELD OF THE INVENTION

This invention relates to novel fluorinated aminobutyric acid and diamino-butane compounds having the following general formula:

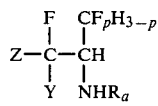

wherein:
Y represents hydrogen or fluorine;
Z represents $-CH_2NR_1R_2$, where $R_1$ and $R_2$ are as defined below, or $-COR_3$ where $R_3$ is as defined below;
$R_a$ represents hydrogen or $R_4$, where $R_4$ is as defined below;
$R_1$ represents hydrogen, $C_1-C_6$ alkyl or phenyl-($C_1-C_4$ alkyl);
$R_2$ represents hydrogen, $C_1-C_6$ alkyl, phenyl-($C_1-C_4$ alkyl) or, when $R_a$ is hydrogen, $R_4$, where $R_4$ is as defined below:
$R_3$ represents hydroxy, or when $R_a$ is hydrogen, $C_1-C_8$ alkoxy, $-NR_5R_6$, where $R_5$ and $R_6$ are as defined below, or an aminocarboxylic acid residue derived by removal of an hydrogen atom from the amino moiety of an L-aminocarboxylic acid;
each $R_4$, independently, represents $C_2-C_5$ alkylcarbonyl, phenylcarbonyl, phenyl-($C_1-C_4$ alkyl)carbonyl, or an aminocarboxylic acid residue derived by removal of an hydroxy group from the carboxy moiety of an L-aminocarboxylic acid;
$R_5$ and $R_6$, independently, represent hydrogen or $C_1-C_4$ alkyl; and
P represents 1 or 2.

The fluorinated amino-butyric acid and diamino-butane compounds in vivo are inhibitors of gamma-aminobutyric acid transaminase (GABA-T). The invention also provides pharmaceutical compositions comprising said compounds, methods of medical treatment using said compounds, and processes for preaparing said compounds.

BACKGROUND OF THE INVENTION

The biotransformation of gamma-aminobutyric acid (GABA) to succinic acid semialdehyde, which is catalyzed by the enzyme GABA-transaminase (GABA-T), is the primary reaction responsible for the catabolism of GABA, an inhibitory neurotransmitter of the central nervous system. It is known that low levels of endogenous GABA are associated with seizures disorders (such as those produced by epilepsy, alcohol withdrawal, or barbiturate withdrawal), with disorders involving involuntary movement (such as Huntington's chorea, the extrapyrimidal effects of drugs, for example tardive dyskinesia) and certain psychoses (such as schizophrenia and mania/depression). Blockade of the transformation of GABA to succinic acid semialdehyde, such as by irreversible inhibition of GABA-T, can elevate GABA levels in the central nervous system (CNS) and, thus provides a means for treating those disorders of the central nervous system associated with low GABA levels.

Certain compounds are known to be irreversible inhibitors of GABA-T and thereby to elevate brain levels of GABA, for example fluorinated methyl gamma-aminobutyric acid and certain derivatives thereof (see U.K. Patent Specification No. 2005264A). Further it is disclosed in U.K. Patent Specification No. 2058052A that fluorinated methyl aminopropionic acids and certain derivatives thereof are also irreversible inhibitors of GABA-T.

SUMMARY OF THE INVENTION

The compounds of the invention are represented by the following general Formula I:

wherein:
Y represents hydrogen or fluorine;
Z represents $-CH_2NR_1R_2$, where $R_1$ and $R_2$ are as defined below, or $-COR_3$ where $R_3$ is as defined below;
$R_a$ represents hydrogen or $R_4$, where $R_4$ is as defined below;
$R_1$ represents hydrogen, $C_1-C_6$ alkyl or phenyl-$C_1-C_4$ alkyl;
$R_2$ represents hydrogen, $C_1-C_6$ alkyl, phenyl-$C_1-C_4$ alkyl or, when $R_a$ is hydrogen, $R_4$, where $R_4$ is as defined below;
$R_3$ represents hydroxy, or when $R_a$ is hydrogen, $C_1-C_8$ alkoxy, $-NR_5R_6$, where $R_5$ and $R_6$ are as defined below, or an aminocarboxylic acid residue derived by removal of a hydrogen atom from the amino moiety of an L-aminocarboxylic acid;
each $R_4$ independently represents $C_2-C_5$ alkylcarbonyl, phenylcarbonyl, phenyl-($C_1-C_4$ alkyl) carbonyl, or an aminocarboxylic acid residue derived by removal of an hydroxy group from the carboxy moiety of an L-aminocarboxylic acid;
$R_5$ and $R_6$ independantly represent hydrogen or $C_1-C_4$ alkyl; and
p represents 1 or 2.

Pharmaceutically acceptable salts of the compounds of Formula I and individual optical isomers of the compounds of Formula I are also included within the scope of the invention.

DETAILED DESCRIPTION OF THE INVENTION

In the above general Formula I, Y represents hydrogen or fluorine, Z represents $-CH_2NR_1R_2$ or $-COR_3$ and p represents 1 or 2. Accordingly, the compounds of Formula I are fluorinated aminobutyric acid or diaminobutane derivatives depending upon whether Z is $-COR_3$ or $-CH_2NR_1R_2$ respectively with a degree of fluorination dependent upon the meaning of Y and the number of p.

In the above general Formula I, $R_a$ can represent hydrogen, $C_2-C_5$ alkylcarbonyl, phenylcarbonyl, phenyl-($C_1-C_4$ alkyl)carbonyl, or an aminocarboxylic acid residue derived by removal of an hydroxy group from the carboxy moiety of an L-aminocarboxylic acid. Preferably $R_a$ represents hydrogen.

In the above general Formula I, $R_1$ and $R_2$ can be the same or different and can represent hydrogen, $C_1-C_6$, preferably $C_1-C_4$, alkyl, phenyl-$C_1-C_4$ alkyl, preferably benzyl or phenethyl or, in the case of $R_2$ only and when $R_a$ is hydrogen, $C_2-C_5$ alkylcarbonyl, phenylcarbonyl, phenyl-($C_1-C_4$ alkyl)carbonyl, or an aminocarboxylic acid residue derived by removal of an hydroxy group from the carboxy moiety of an L-aminocarboxylic acid. Preferably both $R_1$ and $R_2$ represent hydrogen.

In the above general Formula I, $R_3$ represents hydroxy, or, when $R_a$ is hydrogen, $C_1-C_8$ alkoxy, —$NR_5R_6$ or an aminocarboxylic acid residue derived by removal of a hydrogen atom from the amino moiety of an L-aminocarboxylic acid. Said $R_5$ and $R_6$ independently represent hydrogen or $C_1-C_4$ alkyl. Preferably $R_3$ represents hydroxy or $C_1-C_8$ alkoxy.

When $R_3$ is an aminocarboxylic acid residue, it is preferably of the formula —$NHCH(R_7)CO_2H$, wherein $R_7$ is hydrogen, $C_1-C_4$ alkyl, aminopropyl, aminobutyl, benzyl or p-hydroxybenzyl. Similarly, when $R_4$ is an aminocarboxylic acid residue, it can be, for example, of the formula —$COCH(R_7)NH_2$ or —$CO(CH_2)_nCH(NH_2)CO_2H$ wherein $R_7$ is as defined above and n is 1 or 2. Examples of aminocarboxylic acids from which said residues are derived include glycine, alanine, leucine, lysine, isoleucine, phenylalanine, tyrosine, gluatamic acid and aspartic acid.

Reference in this Specification, including the Claims to an alkyl group or moiety means a straight or branched chain alkyl group or moiety and, in the case of an alkyl group or moiety having structural isomers, includes all of those isomers and mixtures thereof unless a particular isomer is specified or clearly implied by the context.

Illustrative examples of straight or branched chain alkyl groups or moieties having 1 to 4 carbon atoms are methyl, ethyl, n-propyl, iso-propyl and n-butyl.

Illustrative examples of straight or branched chain alkyl groups or moieties having 1 to 6 carbon atoms are those specified above having 1 to 4 carbon atoms and n-pentyl, neo-pentyl, n-hexyl and iso-hexyl.

Illustrative examples of straight or branched chain alkyl groups or moieties having 1 to 8 carbon atoms are those specified above having 1 to 6 carbon atoms and n-heptyl, 5-methylhexyl and n-octyl.

Illustrative examples of pharmaceutically acceptable salts of the compounds of this invention include non-toxic acid addition salts formed with inorganic acids, such as hydrochloric, hydrobromic, sulfuric and phosphoric acid, or with organic acids, such as organic carboxylic acids, for example salicylic, maleic, malonic, tartaric, citric and ascorbic acids and organic sulfonic acids, for example, methane sulfonic acid; and non-toxic salts formed with inorganic or organic bases, such as, hydroxides of alkali metals, for example, sodium, potassium and lithium, alkaline earth metals, for example, calcium and magnesium, light metals of Group III A, for example, aluminium, organic amines, such as, primary, secondary or tertiary amines, for example, cyclohexylamine, ethylamine, methylamino-ethanolamine and piperidine. The salts are prepared by conventional means.

In one embodiment of the invention, there are provided compounds of the following general Formula 1A:

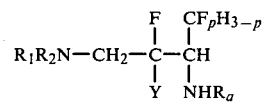
Formula IA wherein:
$R_a$, $R_1$, $R_2$, Y and p are as defined in connection with Formula I.

In another embodiment of the invention, there are provided compounds of the following general Formula IB:

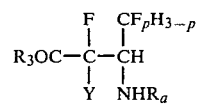
Formula IB wherein:
$R_a$, $R_3$, Y and p are as defined in connection with Formula I.

Illustrative compounds of the invention are the following:
1,3-difluoro-2,4-diamino-butane;
1,1,3-trifluoro-2,4-diamino-butane;
1,3,3-trifluoro-2,4-diamino-butane;
1,1,3,3-tetrafluoro-2,4-diamino-butane;
2,4-difluoro-3-amino-butyric acid;
2,2,4-trifluoro-3-amino-butyric acid;
2,4,4-trifluoro-3-amino-butyric acid;
2,2,4,4-tetrafluoro-3-amino-butyric acid;
1,3,3-trifluoro-2-amino-4-ethylamino-butane;
1,1,3-trifluoro-2-amino-4-diethylamino-butane;
1,3,3-trifluoro-2-(1-oxopropylamino)-4-aminobutane;
N-(1,3-difluoro-4-amino-2-butyl)butyramide;
N-(1,3,3-trifluoro-4-amino-2-butyl)-2-aminoacetamide;
1,3,3-trifluoro-2-amino-4-benzylamino-butane;
ethyl 2,4-difluoro-3-amino-butyrate;
tert.-butyl-2,4-difluoro-3-amino-butyrate;
n-hexyl-2,4,4-trifluoro-3-amino-butyrate;
2,4-difluoro-3-amino-butyramide;
N-ethyl-2,4-difluoro-3-amino-butyramide;
N-N-diethyl-2,4-difluoro-3-amino-butyramide;
N-carboxymethyl-2,4-difluoro-3-amino-butyramide;
N-(1-carboxyethyl)-2,4-difluoro-3-aminobutyramide;
N-($\beta$-phenethyl)-2,4-difluoro-3-amino-butyramide; and
N-($\beta$-4-hydroxyphenylethyl)-2,4-difluoro-3-amino-butyramide;

The compounds of Formula I in vivo produce irreversible inhibition of GABA-T and can elevate GABA levels significantly in the CNS when administered orally or parenterally to warm blooded animals. Thus, the compounds of Formula I are useful for treating disorders in warm blooded animals associated with low levels of GABA in the CNS. For example, the compounds of Formula I are useful as anti-convulsants for the control of seizures involved in epilepsy (grand mal and petit mal), alcohol withdrawal, and barbiturate withdrawal. The anti-convulsant activity of the compounds can be demonstrated by means of standard test procedures in laboratory animals against experimentally-induced seizures. For example, the compounds of Formula I protect mice against clonic seizures induced by bicuculline, when treated according to the procedure of W. Buckett (*Br. J. Pharm.*, 68, 177 (1980)) and *Journal of Pharmacological Methods*, 5, 35 (1981)). The compounds can also protect mice and rats against seizures induced by metrazol (clonic and tonic), maximal electroshock (tonic), and 3-mercaptopropionic acid (clonic and tonic).

It should be recognized that certain compounds of Formula I have shown toxic effects involving convulsions and weight loss ending eventually in death, when administered to mice at certain dosage levels (by single or chronic dosages). However, a significant and physiologically useful increase in GABA levels can be demonstrated experimentally in mice at chronic dosages where no lethal toxicity is observed. The dose responses after chronic administration of 2,4-difluoro-3-amino-butyric acid with respect to the elevation of brain GABA in mice and the toxicity are shown in Example 4.

In addition to the anti-convulsant uses, the compounds of Formula I are useful for treating CNS disorders involving unvoluntary movement, for example tardive dyskinesia, and/or for treating psychoses, for example schizophrenia and mania/depression. Moreover, the compounds of Formula I produce hypothermia, myorelaxation, anorexia, sedation and/or antinociception when administered systemically.

The dosage of the compounds of Formula I in warm blooded animals will depend upon the particular compound employed, the severity of the condition being treated, and the mode of administration. In general, an effective dosage capable of providing physiological useful elevation of GABA levels in the CNS can be achieved in warm blooded animals at a dose of from about 0.1 mg/kg to about 2.0 mg/kg (body weight) per day administered orally or parenterally. Therapy should be initiated at lower doses, the dosage thereafter being increased in very small increments until the desired effect is achieved.

The GABA-T inhibitory activity of the compounds can be demonstrated in laboratory animals in vivo by the methods of M. Jung et al., *J. Neurochem.*, 28, 717 (1977). In human subjects, GABA-T inhibition can be measured after systemic drug administration by determining elevated GABA levels and homocarnosine levels in cerebrospinal fluid (CSF), since there is a known correlation between GABA levels in the brain and GABA levels and homocarnosine level in CSF.

The compounds of Formula I wherein $R_a$, $R_1$, or $R_2$ is a group other than hydrogen, or $R_3$ is a group other than hydroxy, do not inhibit GABA-T in vitro. In order to produce inhibition of GABA-T in vivo such compounds must undergo biotransformation to a compound of Formula I in which $R_a$ is hydrogen and Z is $CH_2NH_2$ or $—CO_2H$.

The compounds of this invention can be administered in various manners to achieve the desired effect. The compounds can be administered alone or in the form of pharmaceutical preparations to the patient being treated either orally or parenterally, for example, subcutaneously, intravenously or interperitoneally. The amount of novel compound administered will vary and can be any effective amount. Unit doses of these compounds can contain, for example, from about 1 mg to 50 mg of the compounds and may be administered, for example, from 1 to 4 times daily.

As used herein the term patient is taken to mean warm blooded animals, such as, humans and other mammals, for example, cats, dogs, rats, mice, guinea pigs, sheep, horses, and Bovine cows.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

In the composition aspect of the invention there are provided pharmaceutical formulations in which form the active compounds of the invention will normally be utilized. Such formulations are prepared in a manner well known per se in the pharmaceutical art and usually comprise at least one active compound of the invention in admixture or otherwise in association with a pharmaceutically acceptable carrier or diluent therefor. For making these formulations the active ingredient will usually be mixed with a carrier, or diluted by a diluent, or enclosed or encapsulated in a capsule, sachet, cachet, paper or other container. A carrier or diluent may be solid, semi-solid or liquid material which serves as a vehicle, excipient or medium for the active ingredient. Suitable diluents or carriers are well known per se.

The formulations of the invention may be adapted for enteral or parenteral use and may be administered to the patient in the form of tablets, capsules, suppositories, solutions, suspensions or the like.

In the specific examples included hereinbelow illustrative examples of suitable pharmaceutical formulations are described.

Methods of preparing the compounds of Formula I will now be described. If in any of the reaction steps described an amino group of a reactant would be involved in an unwanted reaction under the relevant reaction conditions, the amino group will be protected in manner known per se by introduction of an appropriate protecting group. The protecting group will be chosen having regard to the nature of the relevant reaction and ease of removal to free the amino group. The protecting group can be selected from, for example, acyl, for example lower alkanoyl, e.g. acetyl, propionyl, trifluoroacetyl, and the like; aroyl, e.g. benzoyl, toluoyl and the like; lower alkoxycarbonyl, for example methoxycarbonyl, ethoxycarbonyl, tert-butoxycarbonyl and the like; carbobenzoxy, benzene-sulfonyl and tosyl. Both amino hydrogen atoms can be substituted by a single protecting group such as, for example phthalyl. The protection groups are introduced in manner known per se by, for example, reaction of the amine with a lower alkanoyl or aroyl chloride, anhydride, sulfonylchloride, tert-butoxycarbonyloxyimino-2-phenylacetonitrile (BOC-ON), or di-tertiobutyl dicarbonate ($(BOC)_2O$).

Removal of the protection group after the required reaction has been completed can be carried out in manner known per se for the relevant protecting group. Usually, said removal will be by hydrolytic cleavage using a strong organic or mineral acid such as, for example, trifluoroacetic acid, hydrochloric acid and the like acids; by catalytic hydrogenation using Pd or Pt catalyst; or by hydrogen chloride gas under anhydrous conditions. Solvents used will be chosen dependent upon the conditions of protecting group removal. For example, ethers such as, for example, diethylether can be used for cleavage using hydrogen chloride gas.

Compounds of Formula IA in which $R_1$ and $R_2$ are both hydrogen and $R_a$ is hydrogen can be prepared from the corresponding compound of Formula II by conversion in manner known per se of the hydroxy group into a primary amino group.

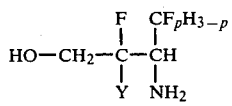
Formula II wherein Y and p are as defined in connection with Formula I.

The conversion of the hydroxy group into a primary amino group can proceed via an amino-protected derivative of the phthalimido compound of the following general Formula III:

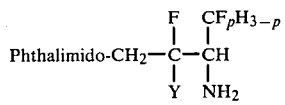
Formula III wherein Y and p are as defined in connection with Formula II.

The phthalimido compound of Formula III can be obtained in manner known per se by treating the compound of Formula II with phthalimide in the presence of a trialkyl- or triarylphosphine and diethyl azodicarboxylate in an anhydrous aprotic solvent. Conveniently, the phosphine is tri-n-butylphosphine or triphenylphosphine and the aprotic solvent is diethyl ether, tetrahydrofuran, dioxane, benzene or dimethoxyethane.

The phthalimido group can be converted in manner known per se into the required primary amino group by hydrolytic cleavage with a strong mineral acid such as, for example, hydrobromic or hydrochloric acid, or by reaction with hydrazine or methylamine;

The preferred protecting group is benzyl or benzhydryl (i.e. diphenylmethyl) which can be removed by catalytic hydrogenolysis in a protic solvent. Suitably palladium on charcoal or platinum oxide can be used as the catalyst and ethanol or acetic acid as the solvent. Preferably, the hydrogenolysis is conducted in the presence of a strong acid, such as, for example hydrochloric acid.

The compound of Formula II can be obtained by reduction in manner known per se of the corresponding acid or ester of the following general Formula V or an amino-protected derivative thereof:

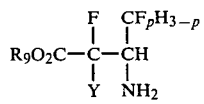
Formula V wherein:
Y and p are as defined in connection with Formula II, and
$R_9$ represents hydrogen, $C_1-C_8$ alkyl or benzyl.

The reduction usually will be carried out using a reducing agent known to reduce carboxylic acid esters to alcohols, preferably diborane in an anhydrous aprotic organic solvent.

The acids and alkyl esters of Formula V are compounds of the invention within the scope of Formula IB.

The compound of Formula V can be obtained by reduction in manner known per se of the corresponding compound of the following general Formula VI or an amino-protected derivative thereof

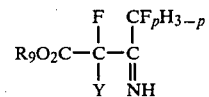
Formula VI wherein Y, p and $R_9$ are as defined in connection with Formula V and, if required, subsequent acid hydrolysis of the ester product of Formula V to the corresponding acid of Formula V. When Y is hydrogen, the compound of Formula VI is tautomeric with the compound of the following Formula VIA:

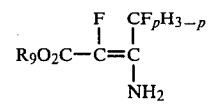
Formula VIA

The reduction can be carried out at acidic pH in a protic solvent using a borohydride salt such as sodium cyano-hydrido borate.

The compound of Formula VI can be prepared in manner known per se from the correspoding fluorinated aceto-acetate of the following general Formula VII

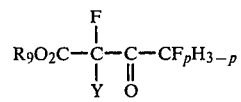
Formula VII wherein Y, p and $R_9$ are as defined in connection with Formula V.

The fluorinated aceto-acetate can be converted into the compound of Formula VI by treatment with the corresponding amine, for example benzylamine or benzhydrylamine in the presence of a catalytic amount of strong acid or by treatment with an excess of ammonium acetate in anhydrons methanol.

The fluorinated aceto-acetates of Formula VII either are known or can be prepared by analogous methods to those reported for the preparation of the known fluorinated aceto-acetates (see, for example, Bergman et al, J. Chem. Soc. (1959), 3278; McBee et al, J. Amer. Chem. Soc. 75 (1953), 3152; and Inman et al, J. Amer. Chem. Soc. 80 (1958), 6533).

Compounds of Formula IA in which $R_a$ is hydrogen and $R_1$ and $R_2$ independently represent hydrogen, $C_1-C_4$ or phenyl-$C_1-C_4$ alkyl but at least one of them is other than hydrogen can be prepared by reducing in manner known per se the corresponding amide of the following general Formula IX or an amino-protected derivative thereof:

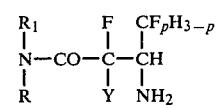
Formula IX wherein:
Y and p are as defined in connection with Formula I; and
$R_1$ and $R_2$ are as defined above.

The reduction can be carried out in an aprotic solvent using a reducing agent such as, for example, a boron hydride, e.g. diborane, an alkyl or alkoxy aluminium hydride, e.g. diisobutyl aluminium hydride, or lithium aluminium hydride.

The compounds of Formula IX can be obtained in manner known per se from the corresponding acid of the following general Formula X or an amino-protected derivative thereof:

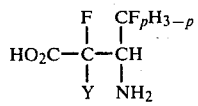

Formula X wherein Y and p are as defined in connection with Formula I.

The compounds of Formula X can be treated with the required amine (i.e. NHR$_1$R$_2$) in an aprotic solvent in the presence of a coupling reagent such as, for example, dicyclohexylcarbodiimide or N-ethoxycarbonyl-2-ethoxy-1,2-dihydroquinoline.

The acids of Formula X are of acids of Formula IB and the preparation of said acids is described hereinafter.

The amides of Formula IA can be prepared directly or indirectly in manner known per se from the corresponding diamines of Formula IA. In some circumstances, it may be necessary to protect the non-reacting amino group prior to the reaction.

If the amide is to be formed at the 2-position (i.e. R$_a$ is to be other than hydrogen), the amino group at the 4-position (i.e. R$_1$ and R$_2$ are both hydrogen) can be protected by forming a phthalimido derivative by, for example, reaction in manner known per se with a (C$_2$-C$_5$ carbalkoxy)phthalimide, e.g. carbethoxyphthalimide. When required, the phthalyl protecting group can be removed by, for example, treatment with hydrazine or methylamine.

If desired, the phthalimido derivative can be obtained directly from a compound of Formula III in which the primary amino group is substituted by benzyl or benzhydryl by catalytic hydrogenolysis in a protic solvent to remove the benzyl or benzhydryl group and thereby free the 2-amino group. Said catalytic hydrogenolysis has been discussed above in connection with conversion of a compound of Formula IV to the corresponding diamine of Formula IA.

If the amide is to be formed at the 4-position, the primary amino group at the 2-position can be protected for example with a benzoxycarbonyl group introduced by reaction in manner known per se with a benzyl haloformate, e.g. benzyl chloroformate. When required, the benzoxy group can be removed by acid hydrolysis, for example by treatment with hydrogen bromide in dioxane.

Amides of Formula IA can be prepared by N-acylating the corresponding compound having a primary amino group by treatment with an acid halide of the formula R$_{10}$CO halogen wherein R$_{10}$ represents C$_1$-C$_4$ alkyl, phenyl or phenyl(C$_1$-C$_4$ alkyl). Conveniently, the reaction is conducted in water in the presence of a base.

In the case where the said amide has an aminocarboxylic acid residue, the amide can be prepared by N-acylation of the corresponding compound having a primary amino group with the corresponding aminocarboxylic acid or an anhydride thereof in which acid or anhydride the amino group is protected with a suitable blocking group such as benzoxycarbonyl or tert-butoxycarbonyl in an anhydrous organic solvent and, when the free acid is employed, in the presence of a dehydrating agent, followed by acid or base hydrolysis.

The preparation of compounds of Formula IB in which R$_a$ is hydrogen and R$_3$ is hydroxy or C$_1$-C$_8$ alkoxy has been described above with reference to the preparation of compounds of Formula V.

An ester of Formula V can be hydrolysed in manner known per se to the corresponding acid (R$_9$ is hydrogen), for example by treatment with aqueous acid, preferably aqueous acetic acid.

The ester and amide derivatives of Formula IB can be prepared directly or indirectly in manner known per se from the acids of Formula IB in which R$_a$ represents hydrogen.

The esters of Formula IB (i.e. R$_3$ is C$_1$-C$_8$ alkoxy) can be obtained in manner known per se from the corresponding acids of Formula IB (i.e. R$_3$ is hydroxy) by conversion into the corresponding acid halide and alcoholysis of said acid halide with the corresponding alkanol. Suitably, the acid halide is the acid chloride prepared by treatment of the acid with thionyl chloride.

The amides of Formula IB wherein R$_3$ represents —NR$_1$R$_2$ can be obtained in manner known per se from the acids of Formula IB (i.e. R$_3$ is hydroxy), in which any free amino group is protected, by conversion into the corresponding acid halide, especially the acid chloride, and subsequent acylation by said acid halide of the corresponding amine (i.e. HNR$_1$R$_2$) or, when R$_1$ and R$_2$ are both hydrogen, ammonia or a compound which is a potential source of ammonia such as an ammonium salt, for example ammonium chloride, in the presence of a base such as triethylamine. Any amino protecting group is subsequently removed, for example by treatment with hydrogen bromide in dioxane or by hydrogenolysis.

In the case where the acid amide has an aminocarboxylic acid residue, the amide usually will be prepared by acylating the corresponding acid of Formula IB or a functional derivative thereof such as an acid anhydride, after, if necessary, protecting any free amino group, with a C$_1$-C$_4$ alkyl ester of the corresponding aminocarboxylic acid.

A dehydrating agent such as, for example, dicyclohexylcarbodiimide will be present when an acid of Formula IB is acylated.

Amides of Formula IB (i.e. R$_a$ is other than hydrogen) can be obtained from the corresponding compounds of Formula IB in which R$_a$ represents hydrogen by the methods of forming amides described above in connection with the preparation of the analogous compounds of Formula IA. In particular, the amine group can be N-acylated with an acid halide, or an aminocarboxylic acid or anhydride thereof.

The individual optical isomers of the compounds of Formula I wherein R$_a$ is hydrogen and Z is carboxy or alkoxycarbonyl can be resolved using a chiral acid such as (+) or (−) binaphthylphosphoric acid salt by the method described by R. Viterbo et al., in Tetrahedron Letters 48, 4617–4620 (1971) and in U.S. Pat. No. 3,848,030 or (+) camphor-10-sulfonic acid. The thus resolved acids and esters may be employed to prepare the individual isomers of other compounds of the invention in the same manner described hereinabove.

When Y is hydrogen, it is convenient to separate the optical isomers of the intermediate compounds of Formula II by chromatography.

The compounds produced by the foregoing processes may be isolated either per se or as acid addition salts thereof.

The acid addition salts are preferably the pharmaceutically acceptable, non-toxic addition salts with suitable acids, such as those previously referred to in this Specification. Apart from pharmaceutically acceptable acid addition salts, other acid addition salts, such as for example, those with picric or oxalic acid are useful; they may serve as intermediates in the purification of the compounds of the invention or in the preparation of other, for example, pharmaceutically acceptable, acid addition salts, or are useful for identification or characterisation of the bases.

A resulting acid addition salt may be converted into the free compound accoding to known methods, for example, by treating it with an alkali or alkaline earth metal hydroxide or alkoxide, with an alkali or an alkaline earth metal carbonate or hydrogen carbonate, with trialkylamine; or with an anion exchange resin.

A resulting acid addition salt may also be converted into another acid addition salt according to known methods; for example, a salt with an inorganic acid may be treated with a metal salt, for example a sodium, barium or silver salt of an acid in a suitable diluent, in which a resulting inorganic salt is insoluble and is thus removed from the reaction medium. An acid addition salt may also be converted into another acid addition salt by treatment with an anion exchange preparation.

The invention is illustrated by the following non-limiting Examples. All NMR measurements are given on the delta scale (i.e. trimethylsilane=0).

EXAMPLE 1

2,4-DIFLUORO-3-AMINO-BUTYRIC ACID

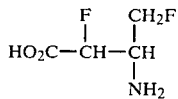

(A) Preparation of: ETHYL 2,4-DIFLUORO-3-BENZYLAMINO-2-BUTENOATE

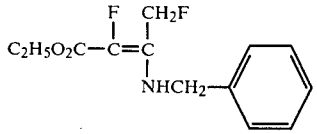

A mixture of ethyl 2,4-difluoro-3-oxo-butanoate (prepared as described in McBee et al J. Amer. Chem. Soc. 75 (1953), 3152) (1.280 g, 7.7 mM), benzyl amine (0.824 g, 7.7 mM), p-toluene sulfonic acid (0.005 g) and benzene (50 ml) is heated at reflux for 20 hours in a flask (100 ml) fitted with a Dean Stark apparatus. The solvent is then evaporated in vacuo yielding a yellow oil. Ethyl 2,4-difluoro 3-benzylamino-2-butenoate is isolated by distillation under reduced pressure: 1.330 g (yield about 68%).

Bp 175° C./0.1 mb (Kugelrohr apparatus).

An approximately 1:1 mixture of cis and trans isomers, as observed by $^1$H NMR spectroscopy.

NMR (CDCl$_3$):1.30 (t, $J_{HH}$=7 Hz, 3H); 4.18 (q, $J_{HH}$=7 Hz); 4.22 (q, $J_{HH}$=7 Hz); 4.40 (AB, $J_{AB}$=16 Hz, $\gamma$AB=15.5 Hz); and 4.50 (s, broad) (5H); 5.13 (dd, $J_{HF4}$=47 Hz, $J_{HF2}$=4 Hz, trans) and 5.47 (dd, $J_{HF4}$=47 Hz, $J_{HF2}$=2 Hz, cis) (2H); 7.20 (s, 5H).

(B) Preparation of: ETHYL 2,4-DIFLUORO-3-BENZYLAMINO-BUTANOATE

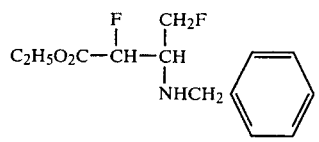

To a solution of ethyl 2,4-difluoro 3-benzylamino-2-butenoate prepared as in Step A (2.265 g, 8.9 mM) in methanol (10 ml) at room temperature is added a trace of bromophenol blue. A 2 N HCl-methanol solution is added until the colour turns yellow. Sodium cyanohydridoborate (prepared as described in Borch et al, J. Amer. Chem. Soc. 93 (1971) 2897) (0.865 g, 13.5 mM) is added with stirring. The 2 N HCl-methanol solution is then added dropwise to maintain the yellow colour. Stirring is continued for 5 hours at room temperature. The solution is poured into 0.1 N sodium hydroxide (15 ml) and the pH adjusted to 10. The aqueous layer is saturated with sodium chloride and extracted three times with ether. The combined extracts are dried over anhydrous magnesium sulfate, and the solvent is evaporated in vacuo yielding a yellow oil. Ethyl 2,4-difluoro-3-benzylamine butanoate is isolated by chromatography (medium pressure silica gel chromatography technique, ethyl acetate/cyclohexane 2:8): 1.240 g (yield about 54%).

NMR (CDCl$_3$): 1.10 and 1.12 (2t, $J_{HH}$=7 Hz, 3H); 1.67 (s, broad, 1H); 2.90-4.00 (m, 3H); 4.18 and 4.20 (2q, $J_{HH}$=7 Hz) and 4.40 (dm, $J_{HF}$=48 Hz) (4H); 4.93 (dm, $J_{HF}$=48 Hz, 1H); 7.22 (s, 5H).

(C) Preparation of: 2,4-DIFLUORO 3-BENZYLAMINO BUTYRIC ACID HYDROCHLORIDE

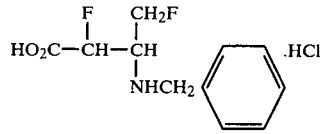

A solution of ethyl 2,4-difluoro-3-benzylaminobutanoate prepared as in Step B (1.240 g, 4.8 mM) in 1 N hydrochloric acid (30 ml) is heated at 100° C. for 4 hours. The solvent is removed in vacuo. The crude product is taken off several times in isopropanol and the alcohol evaporated evaporated in vacuo. 2,4-Difluoro 3-benzylamino-butanoic acid, hydrochloride is obtained as a white solid, recrystallized from ethanol/ether: 1.010 g (yield about 80%).

NMR (D$_2$O): 3.70-4.70 (m, 3H); 4.97 (dm, $J_{HF}$=46 Hz) and 5.50 (dm, $J_{HF}$=46 Hz) (3H); 7.47 (s, 5H).

(D) 2,4-DIFLUORO 3-AMINO BUTYRIC ACID

A mixture of 2,4-difluoro 3-benzylaminobutyric acid, hydrochloride prepared as in Step C (1.010 g, 3.84 mM) and 5% palladium on charcoal (type H, 0.150 g) in glacial acetic acid (30 ml) is shaken under hydrogen (60 psi) in a Parr hydrogenator for 16 hours at room temperature. Filtration of the catalyst, and removal of the solvent in vacuo yield a colourless oil. A first crystal crop was isolated by crystallisation from water/ethanol (0.185 g). A second crystal crop was obtained by passing the mother liquors on an ion exchange column (Dowex 50, H+, eluted with water) (0.190 g). Overall yield about 70%.

Mp: 188° C.

NMR (D20): 3.55–4.30 (m, 1H); 4.75 (dm, $J_{HF}=46$ Hz, 2H); 5.05 (dm, $J_{HF}=46$ Hz, 1H).

EXAMPLE 2

2,4-DIFLUORO-3-AMINO-1-BUTYRIC ACID (A) Preparation of: ETHYL 2,4-DIFLUORO-3-AMINO-2-BUTENOATE

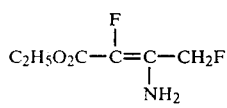

A mixture of ethyl 2,4-difluoro-3-oxobutanoate (24.6 g, 0.148 mol), ammonium acetate (200 g, 2.6 mol) and anhydrous methanol (400 mL) is stirred at room temperature for 3 days. The solution is poured into a saturated aqueous solution of sodium bicarbonate (1L) and extracted four times with ether. The combined organic phases are washed with brine and dried over magnesium sulfate. The solvent is evaporated to yield ethyl 2,4-difluoro-3-amino-2-butenoate (11.1 g, 45%)

(B) Preparation of: 2,4-DIFLUORO-3-AMINO-1-BUTYRIC ACID

To a solution of ethyl 2,4-difluoro-3-amino butenoate (6 g, 0.036 mol) obtained as in Step A in methanol (70 ml) is added a drop of bromophenol blue. A 2 N hydrochloric acid-methanol solution is added until the colour turns yellow. Sodium cyanoborohydride (3.46 g, 0.055 mol) is added with stirring and 2 N hydrochloric acid-methanol solution is added dropwise to maintain the yellow color. Stirring is continued for 4 hours at room temperature and then the solution is poured into sodium dicarbonate, the pH adjusted to 8 and sodium chloride added until saturation. The aqueous solution is extracted three times with ether (3×150 ml) and the combined organic phases are washed with brine and the 1 N aqueous hydrochloric acid (three times). The combined hydrochloric aqueous layers are concentrated in vacuo, concentrated hydrochloric acid is added to the residue and the solution heated at 100° C. for 12 hours. Evaporation of the solvent leaves a residue which is dissolved in water and treated with charcoal. Recrystallization from isopropanol yields 2,4-difluoro-3-amino-1-butyric acid (3 g).

EXAMPLE 3

1,3-DIFLUORO-2,4-DIAMINOBUTANE, DIHYDROCHLORIDE

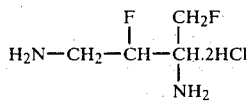

(A) Preparation of: 2,3-DIFLUORO-4-HYDROXY-2-AMINOBUTANE HYDROCHLORIDE

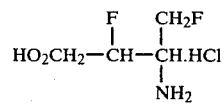

To a suspension of 2,4-difluoro-3-aminobutanoic acid hydrochloride (2 g, 11.4 mmol) in anhydrous tetrahydrofuran (THF) (60 mL) at 0° C. is added a solution of 1 M diborane in THF (57 mL, 57 mmol). The reaction mixture is slowly allowed to warm up to room temperature and, after stirring for 12 hours, methanol (60 mL) is added. The solvent is evaporated in vacuo, the residue dissolved in 1 N hydrochloric acid (40 mL), and the aqueous layer extracted twice with ether. The aqueous phase is concentrated in vacuo and the residue washed several times with THF to afford 1,3-difluoro-4-hydroxy-2-aminobutane hydrochloride (1.8 g).

(B) Preparation of: 1,3-DIFLUORO-2-TERT. BUTOXYCARBONYL-AMINO-4-HYDROXY BUTANE

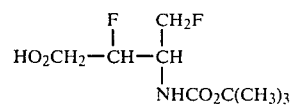

1,3-Difluoror-4-hydroxy-2-aminobutane, hydrochloride (1.3 g, 8 mmol) is dissolved in water (5 mL) and sodium bicarbonate added until the evolution of carbon dioxide ceases. Chloroform (20 mL) and ditert. butylcarbonate (1.75 g), are added to the solution and the mixture heated at 80° C. for 24 hours. The solvents are evaporated in vacuo and the residue taken up in water and extracted with ether. The organic phase is washed with brine, dried over magnesium sulfate and concentrated to give a residue which is purified by column chromatography on silica (eluant ethyl acetate/cyclohexane-2/8) to yield 1,3-difluoro-2-tert.butoxycarbonylamino-4-hydroxybutane (0.755 g) as an oil.

(C) Preparation of: 1,3-DIFLUORO-2-TERT.BUTOXYCARBONYL-AMINO-4-PHTHALIMIDOBUTANE

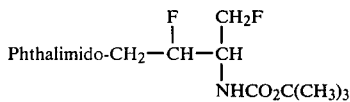

To a solution of 1,3-difluoro-2-tert.butoxycarbonylamino-4-hydroxybutane (0.2 g, 0.83 mmol) obtained as in Step B above in anhydrous THF (8 mL) are added phthalimide (0.122 g, 0.83 mmol), triphenylphosphine (0.217 g, 0.83 mmol) and diethyl azodicarboxylate (0.144 g, 0.83 mmol). The mixture is stirred at room temperature for 24 hours and then the solvents evaporated in vacuo and the residue chromatographed on silicic acid (eluant ethyl acetate/cyclohexane-2/8) to give 1,3-difluoro-2-tert.butoxycarbonylamino-4-phthalimidobutane (150 mg) which is recrystallized from a mixture of ether and pentane. mp 152°–153° C.

NMR (CDCl³): 1.46 (s, 9H), 7.8 (m, 4H), 3.5 to 5.5 (complex m, 6H).

(D) Preparation of:
1,3-DIFLUORO-2,4-DIAMINOBUTANE, DIHYDROCHLORIDE

A mixture of 1,3-difluoro-2-tert.butoxycarbonylamino-4-phthalimidobutane (0.1 g, 0.27 mmol) obtained as in Step C above and concentrated hydrochloric acid is heated at 100° C. for 48 hours. The solvent is evaporated in vacuo and the residue is taken up in water. Insoluble phthalic acid is filtered off and the filtrate concentrated to yield 1,3-difluoro-2,4-diaminobutane, dihydrochloride (0.03 g).

EXAMPLE 4

The ability of the compounds of Formula I to inhibit GABA-T enzyme and to increase GABA concentration in the brain can be demonstrated in the following test procedures in mice.

A group of 10 male albino CD1 mice from Charles Riner, France, is given an i.p. injection of the test compound in aqueous solution daily for four consecutive days. Half of the animals are killed by decapitation 24 hours after the last dose fo the test compound. The other half of the animals are observed for up to 12 days for toxicity (as indicated by weight loss and deaths). Control animals receive an injection of the vehicle only.

The brains are removed from the dead mice and are divided into two portions by sagittal section. One half is used for the measurement of GABA-T activity while the other is used for measuring GABA content. The GABA-T activity is measured using known methods as described by M. Jung et al., J. Neurochem., 28, 717 (1977) and 29, 797 (1977), GABA content is measured by perchloric acid or trichloroacetic acid extracts using an amino acid analyzer equiped with a fluoresence detector.

When tested as described above 2,4-difluoro-3-aminobutyric acid gave the results set forth in Table 1 below:

TABLE 1

| Daily Dose (mg/kg) | GABA-T Inhibition (%) | GABA Elevation (%) | Weight Loss % | Mortality (After Treatment) |
|---|---|---|---|---|
| 1 | 50 | 150 | 0 | 0 |
| 2.5 | 83 | 225 | −5 | 2/5 by day 6 |
| 5 | 87 | 250 | −25 | 5/5 by day 7 |

In the following Examples relating to pharmaceutical compositions, the term "active compound" is used to indicate the compound 2,4-difluoro-3-amino-butric acid. This compound may be replaced in these compositions by any other compound of the invention, for example by 1,3-difluoro-2,4-diaminobutane. Adjustments in the amount of medicament may be necessary or desirable depending upon the degree of activity of the medicament as is well known in the art.

EXAMPLE 5

An illustrative composition for hard gelatin capsules is as follows:
(a) active compound: 20 mg
(b) talc: 5 mg
(c) lactose: 90 mg The formulation is prepared by passing the dry powders of (a) and (b) through a fine mesh screen and mixing them well. The powder is then filled into hard gelatine capsules at a net fill of 115 mg per capsule.

EXAMPLE 6

An illustrative composition for tablets is as follows:
(a) active compound: 20 mg
(b) starch: 43 mg
(c) lactose: 45 mg
(d) magnesium stearate: 2 mg The granulation obtained upon mixing the lactose with the compound (a) and the part of the starch and granulated with starch paste is dried, screened, and mixed with the magnesium stearate. The mixture is compressed into tablets weighing 110 mg each.

EXAMPLE 7

An illustrative composition for an injectable suspension is the following 1 ml ampul for an intramuscular injection:

|  | Weight percent |
|---|---|
| (a) active compound | 1.0 |
| (b) polyvinylpyrrolidone | 0.5 |
| (c) lecithin | 0.25 |
| (d) water for injection to make | 100.0 |

The materials (a)-(d) are mixed, homogenized and filled into 1 ml ampuls which are sealed and autoclaved 20 minutes at 121° C. Each ampul contains 10 mg per ml of novel compound (a).

EXAMPLE 8

|  | mg/suppository |
|---|---|
| Active compound | 50 |
| Oil of Theobroma | 950 |

The medicament is powdered and passed through a B.S. No. 100 Sieve and triturated with molten oil of Theobroma at 45° C. to form a smooth suspension. The mixture is well stirred and poured into moulds each of nominal 1 G capacity, to produce suppositories.

What is claimed is:

1. A compound of the formula:

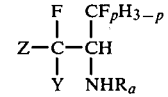

wherein:
Y is hydrogen or fluorine;
Z is —CH$_2$NR$_1$R$_2$, where R$_1$ and R$_2$ are as defined below, or —COR$_3$ where R$_3$ is as defined below;
R$_a$ is hydrogen or R$_4$, where R$_4$ is as defined below;
R$_1$ is hydrogen, C$_1$–C$_6$alkyl or phenyl-(C$_1$–C$_4$alkyl);
R$_2$ is hydrogen, C$_1$–C$_6$alkyl, phenyl-(C$_1$–C$_4$alkyl), or, when R$_a$ is hydrogen, R$_4$, where R$_4$ is as defined below;
R$_3$ is hydroxy, or, when R$_a$ is hydrogen, C$_1$–C$_8$alkoxy, —NR$_5$R$_6$, where R$_5$ and R$_6$ are as defined below, or an aminocarboxylic acid residue derived by removal of an hydrogen atom from the amino moiety of glycine or an L-aminocarboxylic acid of the formula NH$_2$CH(R$_7$)CO$_2$H wherein R$_7$ is $C_1$–$C_4$alkyl, aminopropyl, aminobutyl, benzyl, or p-hydroxybenzyl;

each $R_4$, independently, is $C_2$–$C_5$alkylcarbonyl, phenylcarbonyl, phenyl-($C_1$–$C_4$alkyl)carbonyl, or an aminocarboxylic acid residue derived by removal of an hydroxy group from the carboxy moiety of glycine or an L-aminocarboxylic acid of the formula HO—COCH($R_7$)NH$_2$ or HO—CO(CH$_2$)$_n$CH(NH$_2$)CO$_2$H wherein $R_7$ is $C_1$–$C_4$alkyl, aminopropyl, aminobutyl, benzyl, or p-hydroxybenzyl and n is 1 or 2;

$R_5$ and $R_6$, independently, are hydrogen or $C_1$–$C_4$alkyl; and p is 1 or 2, or a pharmaceutically acceptable salt thereof.

2. A compound as defined in claim 1 of the formula:

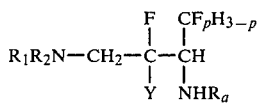

wherein; $R_a$, $R_1$, $R_2$, Y, and p are as defined in claim 1, and pharmaceutically acceptable salts thereof.

3. A compound as defined in claim 2 wherein both $R_1$ and $R_2$ are hydrogen.

4. A compound as defined in claim 3 wherein $R_a$ is hydrogen.

5. The compound as defined in claim 4 which is 1,3-difluoro-2,4-diaminobutane.

6. A compound as defined in claim 3 wherein $R_a$ is $R_4$.

7. A compound as defined in claim 2 wherein $R_a$ is hydrogen.

8. A compound as defined in claim 7 wherein $R_1$ is hydrogen, and $R_2$ is $C_1$–$C_6$alkyl, phenyl-($C_1$–$C_4$alkyl), or $R_4$.

9. A compound as defined in claim 1 having the formula:

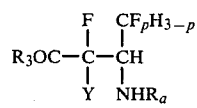

wherein: $R_a$, $R_3$, Y, and p are as defined in claim 1, and pharmaceutically acceptable salts thereof.

10. A compound as defined in claim 9 wherein $R_a$ is hydrogen.

11. A compound as defined in claim 10 wherein $R_3$ is hydroxy.

12. The compound as defined in claim 11 which is 2,4-difluoro-3-aminobutyric acid.

13. A compound as defined in claim 10 wherein $R_3$ is $C_1$–$C_8$alkoxy.

14. A compound as defined in claim 9 wherein $R_3$ is hydroxy and $R_a$ is $R_4$.

15. A compound as defined in claim 1, 2, 3, 4, 6, 7, 8, 9, 10, 11, 13, or 14 wherein Y is hydrogen.

16. A compound as defined in claim 1, 2, 3, 4, 6, 7, 8, 9, 10, 11, 13, or 14 wherein Y is fluorine.

17. A compound as defined in claim 1, 2, 3, 4, 6, 7, 8, 9, 10, 11, 13, or 14 wherein p is 1.

18. A compound as defined in claim 1, 2, 3, 4, 6, 7, 8, 9, 10, 11, 13, or 14 wherein p is 2.

19. A pharmaceutical composition for inhibiting gamma-aminobutyric transaminase comprising an effective amount of a compound as defined in claim 1 and a pharmaceutically acceptable carrier.

20. A pharmaceutical composition as defined in claim 19 wherein the compound is 2,4-difluoro-3-aminobutyric acid or 1,3-difluoro-2,4-diamino butane or a pharmaceutically acceptable salt thereof.

* * * * *